United States Patent [19]

Johnstone

[11] Patent Number: 5,760,395
[45] Date of Patent: Jun. 2, 1998

[54] METHOD AND APPARATUS FOR LASER-CONTROLLED PROTON BEAM RADIOLOGY

[75] Inventor: Carol J. Johnstone, Warrenville, Ill.

[73] Assignee: Universities Research Assoc., Inc., Washington, D.C.

[21] Appl. No.: 634,242

[22] Filed: Apr. 18, 1996

[51] Int. Cl.⁶ .................... H01J 37/30; H05H 3/00
[52] U.S. Cl. ............................. 250/306; 250/251
[58] Field of Search ........................ 250/251, 423 P, 250/492.3, 306

[56] References Cited

U.S. PATENT DOCUMENTS

| | | | |
|---|---|---|---|
| H75 | 6/1986 | Grisham et al. | 376/143 |
| 3,980,885 | 9/1976 | Steward et al. | 250/307 |
| 3,986,026 | 10/1976 | Martin | 250/306 |
| 4,327,288 | 4/1982 | Ashkin et al. | 250/251 |
| 4,649,273 | 3/1987 | Chutjian | 250/423 P |
| 4,870,287 | 9/1989 | Cole et al. | 250/492.3 |
| 4,975,572 | 12/1990 | Rempt | 250/251 |
| 5,089,711 | 2/1992 | Morsell et al. | 250/492.3 |
| 5,099,130 | 3/1992 | Aitken | 250/396 R |
| 5,124,554 | 6/1992 | Fowler et al. | 250/358.1 |
| 5,150,704 | 9/1992 | Tatebayashi et al. | 128/395 |
| 5,151,928 | 9/1992 | Hirose et al. | 378/119 |
| 5,260,581 | 11/1993 | Lesyna et al. | 250/492.3 |
| 5,267,294 | 11/1993 | Kuroda et al. | 378/65 |
| 5,312,395 | 5/1994 | Tan et al. | 606/9 |
| 5,328,488 | 7/1994 | Daikuzono | 606/16 |
| 5,336,217 | 8/1994 | Buys et al. | 606/9 |
| 5,343,224 | 8/1994 | Paoli | 346/108 |
| 5,349,198 | 9/1994 | Takanaka | 250/492.3 |
| 5,353,291 | 10/1994 | Sprangle et al. | 372/5 |

OTHER PUBLICATIONS

"Response to the ¹P° Resonance Near n=3 In the H Continuum to External Electric Fields", 1987 The American Physical Society, vol. 36, No. 10, Stanley Cohen et al.

"Observation of Motional-Field-Induced Ripples In the Photodetachment Cross Section of H⁻", 1987 The American Physical Society, vol. 58, No. 23, H.C. Bryant et al.

(List continued on next page.)

*Primary Examiner*—Bruce Anderson
*Attorney, Agent, or Firm*—McAndrews, Held & Malloy, Ltd.

[57] ABSTRACT

A proton beam radiology system provides cancer treatment and proton radiography. The system includes an accelerator for producing an H⁻ beam and a laser source for generating a laser beam. A photodetachment module is located proximate the periphery of the accelerator. The photodetachment module combines the H⁻ beam and laser beam to produce a neutral beam therefrom within a subsection of the H⁻ beam. The photodetachment module emits the neutral beam along a trajectory defined by the laser beam. The photodetachment module includes a stripping foil which forms a proton beam from the neutral beam. The proton beam is delivered to a conveyance segment which transports the proton beam to a patient treatment station. The photodetachment module further includes a laser scanner which moves the laser beam along a path transverse to the cross-section of the H⁻ beam in order to form the neutral beam in subsections of the H⁻ beam. As the scanning laser moves across the H⁻ beam, it similarly varies the trajectory of the proton beam emitted from the photodetachment module and in turn varies the target location of the proton beam upon the patient. Intensity modulation of the proton beam can also be achieved by controlling the output of the laser.

20 Claims, 5 Drawing Sheets

OTHER PUBLICATIONS

"Stability of the $^1p°$ Shape Resonance in the Moderate Electric Fields", 1987 The American Physical Society, vol. 35, No. 4, G. Comtet et al.

"Production of Pulsed Particle Beams by Photodetachment of H†", 1971 Physical Review Letters, vol. 27, No. 24, H.C. Bryant et al.

"Effects of Electric Fields On the Photodetachment Cross Section of the H Ion Near Threshold", 1988 The American Physical Society, vol. 38, No. 11, J.E. Stewart et al.

"Energy Measurement of the Lowest $^1P°$ Feshbach Resonance In H", 1985 The American Physical Society, vol. 32, No. 3, D.W. MacArthur et al.

"Test of the Special–Relativistic Doppler Formula at $\beta=0.84$", 27 Jan. 1986, Physical Review Letters, vol. 56, No. 4, D. W. MacArthur et al.

"Erratum", 9 Jan. 1984, Physical Review Letters, vol. 52, No. 2, J.B. Donahue et al.

"Observation of Two–Electron Photoionization of the H Ion near Threshold", 31 May 1982, Physical Review Letters, vol. 48, No. 22, J.B. Donahue et al.

"Observation of Narrow Resonances in the H Photodetachment Cross Section near the n=3 Threshold", 3 Dec. 1979, Physical Review Letters, vol. 43, No. 23, M.E. Hamm et al.

"Effect of an Electric Field upon Resonances in the H Ion", 9 Jan. 1978, Physical Review Letters, vol. 40, No. 2, P.A.M. Gram et al.

"Further studies of H photodetachment in electric fields", 1 Jun. 1990, Physical Review A, vol. 41, No. 11, P.G. Harris et al.

"Observation of Resonances near 11 eV in the Photodetachment Cross Section of the H Ion", 31 Jan. 1977, Physical Review Letters, vol. 38, No. 5, H.C. Bryant et al.

"Resonant Two–Photon Detachment through the Lowest Single D State in H", 16 Oct. 1995, Physical Review Letters, vol. 75, No. 16, A. Stintz et al.

"Effects of strong electric fields on resonant structures in H photodetachment", Jun. 1983, Physical Review A, vol. 27, No. 6, H.C. Bryant et al.

"Observation of multiphoton detachment of the H ion", Jun. 1, 1989, Physical Review A, vol. 39, No. 11, C.Y. Tang et al.

"Shape Resonances in the Hydrogen Stark Effect in Fields up to 3 MV/cm", Aug. 20, 1984, Physical Review Letters, vol. 53, No. 8, T. Bergeman et al.

"Implementation of a Low Energy Proton Line from Fermilab Linac", Jul., 1992, Fermilab Technical Memorandum No. TM–1788, Johnstone.

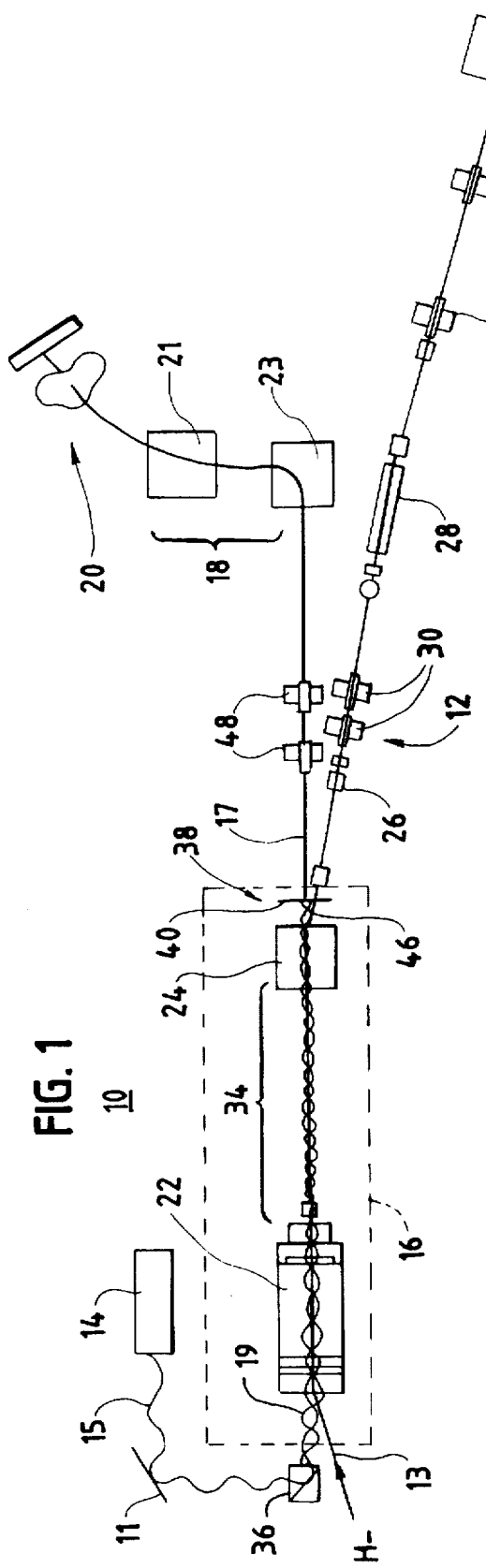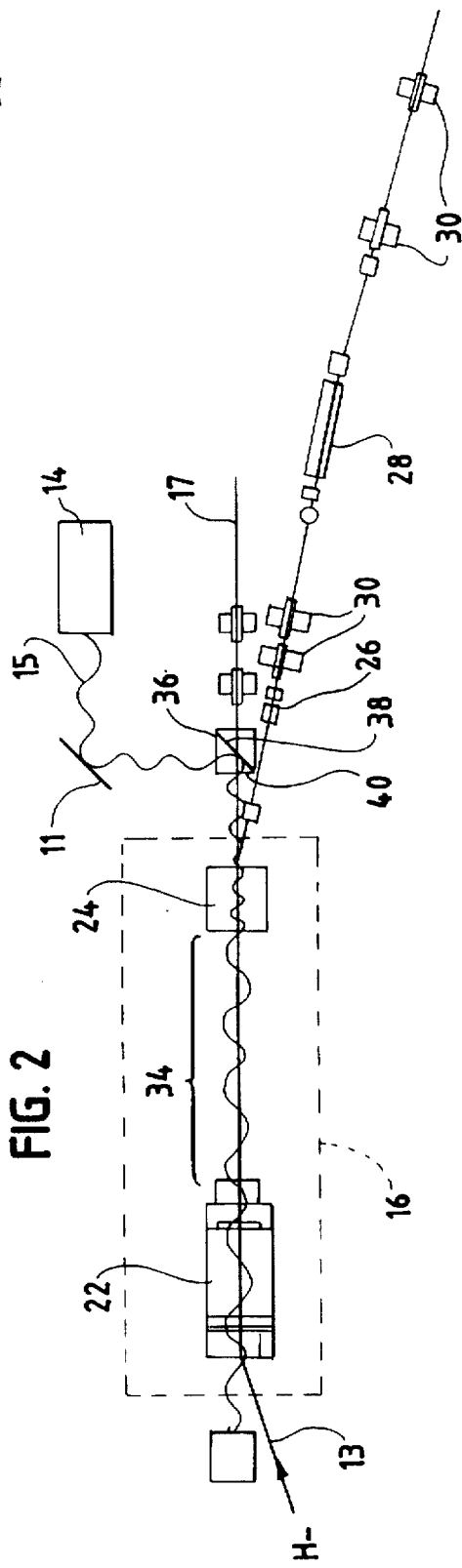

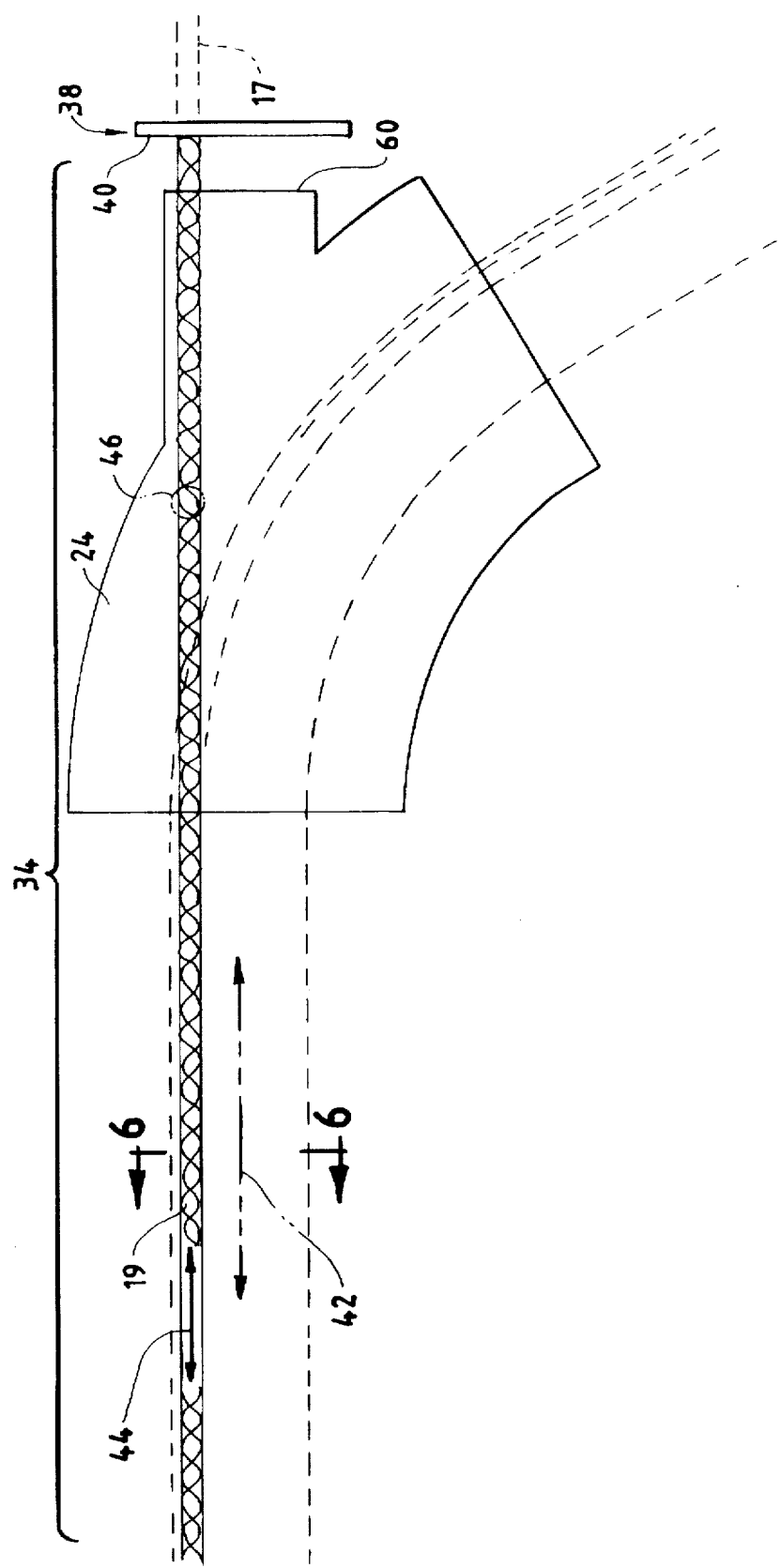

METHOD AND APPARATUS FOR LASER-CONTROLLED PROTON BEAM RADIOLOGY

This invention was made with Government support under Contract No. DE-AC02-76CH03000 awarded by the U.S. Department of Energy. The Government has certain rights in this invention.

FIELD OF THE INVENTION

The present invention generally relates to a proton radiology system for use in proton radiography, proton cardiography, proton irradiation and similar medical applications for diagnosis and treatment of disease. More specifically, the present invention relates to a proton radiology system which employs lasers to effect proton beam guidance and intensity control in order to enhance the system's imaging rate, targeting accuracy and intensity control.

BACKGROUND OF THE INVENTION

Proton beam therapy has only been employed to a limited extent within the medical field. An existing proton beam therapy system is located at the Harvard Cyclotron Laboratory in association with Massachusetts General Hospital in Boston, Mass. Other therapy systems exist or are being planned at institutes across the U.S. and in other countries including Russia, Japan, Italy and Korea.

Conventional systems have been proposed which attempt to more fully realize the potential use of proton beams in the treatment of cancer and other diseases, such as proposed in U.S. Pat. No. 4,870,287. The '287 patent discloses a proton beam therapy system which includes a plurality of separate treatment stations served from a single proton source and proton beam accelerator. At each treatment station, a gantry delivers a proton beam from various angles to a patient supported in a fixed orientation. The proton beam is transported from the accelerator to the patient treatment station through a beam transport system. The transport system includes a gantry at each treatment station and a proton beam switchyard. The switchyard includes proton beam switching magnets which guide the proton beam to a desired station. Rotation of the gantries enables the proton beam to be delivered to the target patient from several different angles during treatment. However, such conventional systems for proton beam therapy have several disadvantages and therefore limited use.

Linear accelerators were originally used primarily in the field of experimental physics. Typically, linear accelerators generate proton beams having extremely high output intensities. Such intensities were desirable in experimental physics research. However, the beam intensity must be significantly reduced to be safely employed within the medical field for human radiography and irradiation therapy, since beam intensity controls the dosage of an associated treatment. Dosage must, therefore, be controlled precisely. It is thus important to provide the ability to vary the beam intensity by extremely small amounts and with high accuracy.

The control of beam intensity is further complicated in view of the production by linear accelerators of discrete bursts of $H^-$ beams and an inherent pulse-to-pulse intensity variation between pulses in the incident $H^-$ ion beam. Consequently, intensity variations are also produced in the resulting proton beam. In the field of particle physics, these intensity variations are more readily accounted for and do not have a significant detrimental effect upon the research. However, within the medical field, it is extremely important to uniformly radiate the targeted subject with a proton beam and to regulate the dosage delivered. Accordingly, it is extremely important to modulate the intensity of the treatment proton beam independent of the output intensity of the accelerator. Instantaneous correction of intensity variations allows the dosage delivered to be controlled to within the prescribed limits.

To achieve adequate intensity control, conventional proton beam therapy systems require extremely complex components and structures. Such conventional intensity controls are imposed directly on the physical operation of the accelerator and result in an inefficient use of the beam. As much as half of the proton beam in an accelerator may be wasted in order to achieve accurate dose rates.

Further, a conventional system has been proposed for proton radiography (as disclosed in U.S. Pat. No. 3,986,026) which affords the ability to produce images of tissue, organs and tumors in a human patient. The medical proton radiography system includes a synchrotron which accelerates a source of negative hydrogen ($H^-$) ions to an energy in the range of 200–600 MeV. A plurality of stripping stations are provided for converting the $H^-$ ions to $H^+$ ions (i.e., hydrogen protons) while maintaining same in a fine beam. The proton beam is passed through a sweeping mechanism which guides the beam along a raster pattern covering a desired area of a human patient. The sweeping mechanism includes a magnetic coil that operates in a manner similar to a conventional magnetic sweeping coil within a television. A control current is supplied to the sweeping magnet coil in a manner necessary to continuously redirect the proton beam as it passes through the coil along a sweeping raster.

A detection device is located on a side of the patient opposite the incident proton beam and is irradiated by the proton beam as it passes through the patient. The proton beam changes energy as it passes through the patient. The energy changes are associated with different types of tissue within the patient. A display device interprets the detected signals and produces a proton radiogram of the tissue.

Conventional radiography systems have been unable, however, to provide an extremely fast scanning rate and thus have limited the use of proton radiography. For instance, conventional systems are unable to perform cardiography, namely, the imaging of heart activity, since they are unable to scan fast enough. To effect cardiography, an imaging system must be able to generate approximately 10 images of the heart per beat which translate into a scanning rate of approximately 20 images of the heart per second. Existing proton imaging systems are unable to achieve this scanning rate since these systems use scanning magnets to control the raster pattern movement of the proton beam. Conventional scanning magnets are generally only able to move the beam at an intermediate speed. While fast magnets are used in high energy laboratories for studying particle physics, such magnets are unable to control raster scanning of a proton beam without overheating. In experimental physics facilities, fast magnets are designed to control proton or ion beams during the acceleration cycle of an accelerator. The discrete and intermittent demands placed upon such magnets require that the magnet operate at a predefined instant followed by a long delay, thereby forming an extremely low repetition rate or duty cycle. Fast magnets are not required to operate continuously in physics research for long periods of time.

In contrast, within the field of medical proton radiography, the proton beam operates substantially continu-

3 ously and thus the conventional scanning magnets must continuously operate to achieve the raster movement. Slower magnets are required to overcome excessive power consumption and heating problems. Therefore, conventional proton radiography systems have not achieved extremely high imaging rates to date.

Finally, in the field of experimental physics, it has been shown that an H⁻ beam may be converted to a neutral (H°) beam when irradiated with a laser beam of sufficient energy. Such experiments are discussed in several publications, such as, for example, P. G. Harris et al., "Further Studies of H⁻ Photodetachment in Electric Fields", published by the *American Physical Society*, 1990, Volume 41, No. 11, pages 5968–5973, which is incorporated herein by reference in its entirety. Another publication related to laser based photodetachment is C. Johnstone, "Implementation of a Low Energy Proton Line From the Fermilab Linac", Fermi National Accelerator Laboratory, P.O. Box 500, Batavia, Ill. 60510, which is also incorporated herein by reference in its entirety.

As described in the foregoing publications, an accelerator is provided with a scattering chamber which receives an H⁻ beam along a first axis and a laser beam along a second axis. The laser and H⁻ beams are incident upon one another at a predefined angle. The laser beam is guided along this predefined angle via mirrors. The laser beam emits sufficient energy to detach or strip an electron from each incident negative hydrogen ion. Once photodetachment occurs, a neutral hydrogen beam results, thereby forming an H° beam. The scattering chamber includes dipole magnets positioned along the H⁻ beam downstream of the point of incidence between the H⁻ and laser beams. The dipole magnets deflect the remaining negatively charged portion of the H⁻ beam along a first path. The neutral H° beam travels through the dipole magnets unaffected along a second path, thereby separating the H⁻ and H° beams. The neutral beam is subsequently stripped of the remaining electrons to form a proton beam with the output energy of the Linac, (i.e., 100–400 MeV).

However, the laser based photodetachment system as proposed in the above noted publications has not been implemented in a medical application. Further, the proposed laser based photo detachment system, even if implemented in the medical field, would not overcome the disadvantages of conventional proton therapy and radiography systems discussed above. Specifically, as noted above, excessive variations in the proton beam intensity are of less concern in experimental physics applications than in the medical field. Hence, the proposed laser based system does not address the need, nor include means for, reducing and controlling proton beam intensity sufficiently to facilitate use in proton irradiation therapy of humans. Nor does the proposed laser based system address the need, or include means for, utilizing the laser to induce high speed raster movement of the proton beam to facilitate use in proton radiography of humans. Thus, while it has been proposed within the field of experimental physics that a laser beam is capable of effecting photodetachment in an H⁻ beam, the proposed laser based systems have not yet been extended to produce a system applicable to or useful within the medical field.

In view of the foregoing, a need remains within the medical field for an improved proton radiography system capable of fast imaging, precise targeting control, reduced beam intensity and modulates. It is therefore an object of the present invention to meet this need.

SUMMARY OF THE INVENTION

The above and other objects are achieved by a proton beam radiology system including an accelerator for accelerating H⁻ ions to a desired energy level to produce an H⁻ beam. The system further includes a laser source for generating a laser beam having photons of a predefined energy level. A photodetachment module is provided proximate to and extending along a predefined peripheral portion of the accelerator. The photodetachment module receives the H⁻ beam and the laser beam and projects the laser beam onto a subsection of the H⁻ beam in order to cause photodetachment within the subsection and to form a neutral beam therein. The photodetachment module includes a stripper at its downstream end to produce a proton beam from the neutral beam. The proton beam extends along a trajectory corresponding to that of the neutral beam and defined by the laser beam. The radiology system further includes a conveyance segment for receiving and transporting the proton beam along a trajectory to a medical treatment station which delivers the proton beam to a target location upon a patient. A laser scanner is included and is operative with the photodetachment module to move the scanning laser beam along a transverse scanning pattern within the cross-section of the H⁻ beam. As the laser beam is moved within the H⁻ beam, it similarly adjusts the trajectory of the resulting proton beam and varies the corresponding target location upon the patient at the treatment station. In a proton radiography application, the patient station includes a detection device located on the side of the patient opposite to the incident proton beam. The detection device senses the proton beam as it passes through the patient. The detection device is attached to a display which produces an image of the scanned region of the patient. In a proton irradiation therapy application, the laser beam intensity is varied in order to produce a proton beam having a prescribed dose rate appropriate for the region of the patient to be treated.

BRIEF DESCRIPTION OF THE DRAWINGS

FIG. 1 is in block diagram form a preferred embodiment of the present invention.

FIG. 2 is in block diagram form an alternative embodiment of the present invention.

FIG. 3B is a top plan view of a downstream portion of the photodetachment region.

DETAILED DESCRIPTION OF THE PREFERRED EMBODIMENTS

Figure 3A:
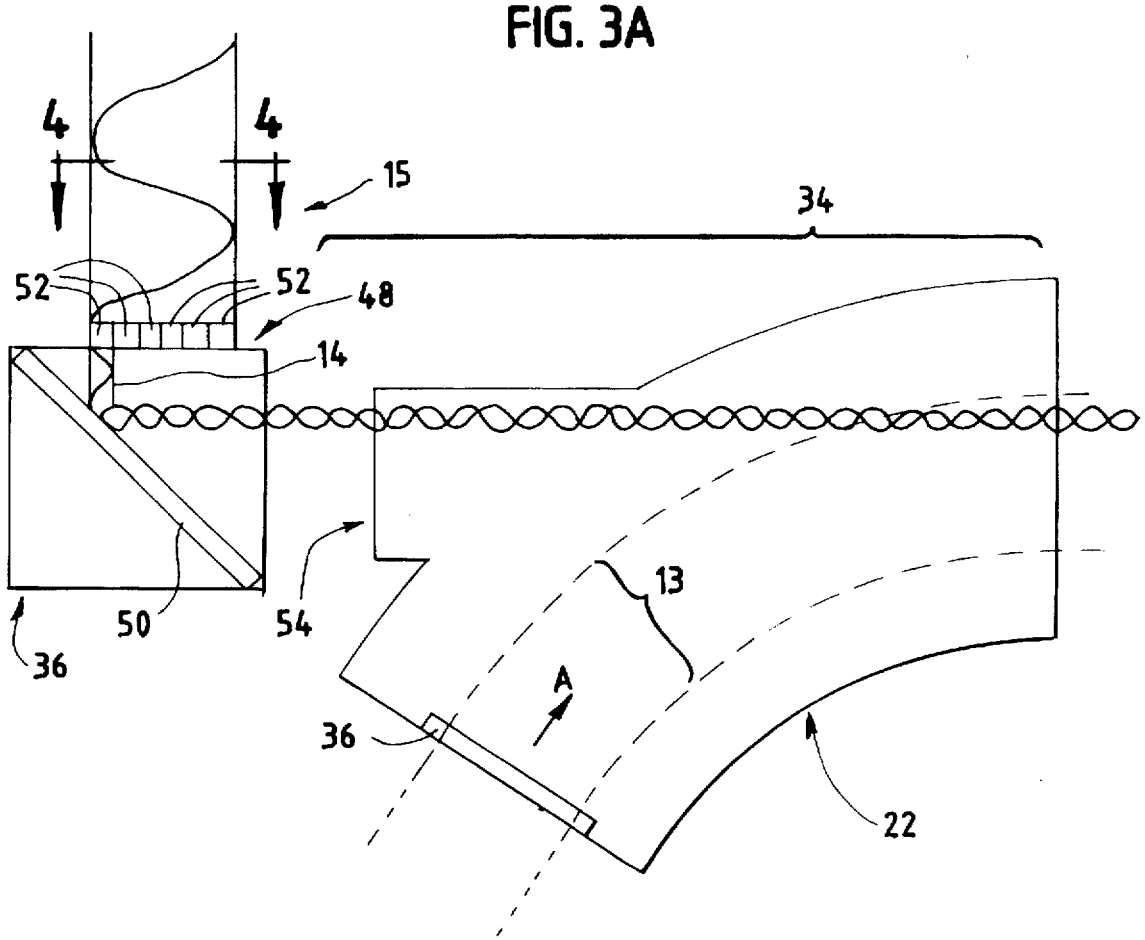
FIG. 3A is a top plan view of an upstream portion of a photodetachment region.

FIG. 1 generally illustrates a radiology system according to the present invention for use in medical treatment, proton radiography, proton cardiography and the like. The radiology system 10 includes an accelerator 12 which receives and accelerates a stream of H⁻ ions to a desired energy level in order to produce a H⁻ beam 13. The accelerator 12 may be a linear accelerator, a synchrotron, a cyclotron, and the like, so long as the accelerator is able to provide H⁻ ions with sufficient energy (e.g. 50–500 MeV). The radiology system 10 further includes a laser source 14 which emits an incident laser beam 15 with a desired energy level sufficient to effect photodetachment as explained below. By way of example, the laser source 14 may emit a laser beam having 1–2 electron volts per photon (corresponding to the peak of the H⁻ photodetachment reaction). Generally, a reliable high power laser may be used, such as a Nd:YAG laser and the like. For higher energy applications, the Doppler shift effect may be used to allow longer wavelength lasers, such as the CO laser to be used (e.g. a 5 micron wavelength or 0.2 eV per photon).

The incident laser beam 15 may be directed by a reflective mirror 11 to a photodetachment module 16 (generally denoted in dashed outline). The photodetachment module 16 produces a proton beam 17 which is delivered to a conveyance module 18. The conveyance module 18 in turn guides the proton beam 17 to a patient treatment station 20, at which the proton beam 17 is delivered to a patient. The treatment station 20 may represent a cancer therapy station at which proton beam irradiates cancer cells. Alternatively, the treatment station 20 may represent a radiography or cardiography station for imaging of a patient for tissue and tumor identification.

FIG. 1 is a schematic of a set up designed for a linear accelerator where diagnostic trim magnets 26, dipole magnets 28, quadrupole magnets 30, and a beam dump 32 are located downstream of the module 16. A scanner unit 36, such as a pockel cell array and/or turning mirror, is located upstream of the module 16. The scanner 36 receives the laser beam 15 incident from the mirror 11 and deflects a portion thereof through the module 16 as a scanning beam 19. The scanner 36 is controlled to move the scanning 19 beam in a transverse manner across the H⁻ beam 13, such as in a raster or discrete targeting pattern.

A stripping foil 38 is included downstream of the module 16. The stripping foil 38 is aligned substantially normal to an axis of the H⁻ beam 13. The foil 38 has a reflective coating 40 on an upstream face thereof. In this particular setup, the reflective coating 40 reflects the scanning beam 19 directly back upon itself along the laser beam's axis. Within the module 16, a photodetachment region 34 extends between bending dipole magnets 22 and 24. The scanning beam 19 within the photodetachment region 34 charge changes a coinciding subsection of the H⁻ beam 13. The charge changed subsection of the H⁻ beam represents a neutral H° beam 46. The neutral beam 46 passes through the module 16 unaffected by the magnetic fields therein and continues along the laser axis. The neutral beam 46 impinges upon the stripping foil 38 and, while passing there through, is converted to a proton beam 17. The proton beam 17 passes through quadrupoles 48 and is delivered to the conveyance module 18 which may include static magnets and the like to guide the proton beam 17 to the treatment station 20.

Turning next to FIGS. 3–6 to explain the photodetachment process in more detail. The module 16 includes first and second bend dipole magnets 22 and 24 spaced apart by a predefined distance (e.g. 1 meter). The photodetachment region 34 extends between these dipole magnets. The first dipole magnet 22 receives an incoming H⁻ beam 13 traveling in the direction indicated by arrow A (FIG. 3A) and redirects the H⁻ beam 13 at its discharge end to travel in a direction parallel to an H⁻ beam axis 42 (FIG. 3B). The scanner 36 includes a pockel cell 48 aligned at an entrance thereto and oriented to receive the incident laser beam 15. The pockel cell 48 includes an array of electro-optic elements 52 (FIG. 4) arranged in a predefined pattern, such as in a rectangle, circle and the like. The electro-optic elements 52 are electrically controlled to switch between optically transmissive and non-transmissive states, in order to individually and selectively pass subsections of the incident beam 15. The scanner 36 controls the optical transmissivity of the pockel cell 48 to pass one or more selected subsections of the incident beam 15. An element 52 may be partially transmissive to vary the intensity of the emitted scanning beam 19.

Figure 4:
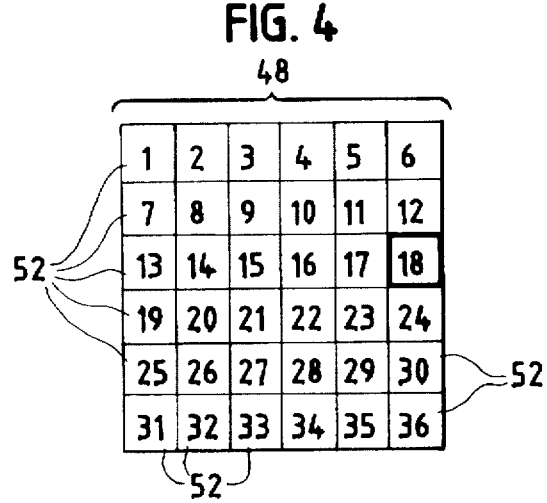
FIG. 4 is a cross-sectional view of a pockel cell arrangement as viewed along line 4—4 in FIG. 3A.

FIG. 4 is an exemplary cross-sectional arrangement for the pockel cell 48. As shown in FIG. 4, the pockel cell 48 may include 36 electro-optic elements individually denoted #1–#36. In the example of FIGS. 3–6, the electro-optic element denoted #18 has been turned on to be optically transmissive. Thus, returning to FIGS. 3A and 3B, pockel cell 48 emits a scanning beam 19 from one (or more) of the electro-optic elements 52. The scanning beam 19 is incident upon the turning mirror 50 and redirected through a port 54 into the bending magnet 22. The scanning beam 19 travels through the photodetachment region 34 along a laser beam axis 44 (FIG. 3B) until contacting the reflective coating 40 upon the stripping foil 38. In this configuration, the coating 40 reflects the laser beam 19 directly back upon itself to travel in reverse direction along the laser beam axis 44 until contacting the scanner 36. The system may be designed to prevent the return laser beam 19 from being retransmitted through the pockel cell 48 and onto the laser source 14. To do so, the return laser beam 19 may be diverted from the laser source 14 by reflecting the return laser beam 19 at a slight angle to the initial forward beam or by rotating polarization of the return laser beam 19. Optionally, a laser source 14 may be used which is able to accept the return laser beam 19.

During the scanning operation, the scanner 36 controls the pockel cell 48 to sequentially turn on and off a sequence of electro-optic elements 52. For instance, in a radiography application, the electro-optic elements 52 could be turned on and off according to the sequence #1, #2, #3, #4, #5, . . . . , #34, #35, #36 to produce a raster scanning pattern.

Figure 5:
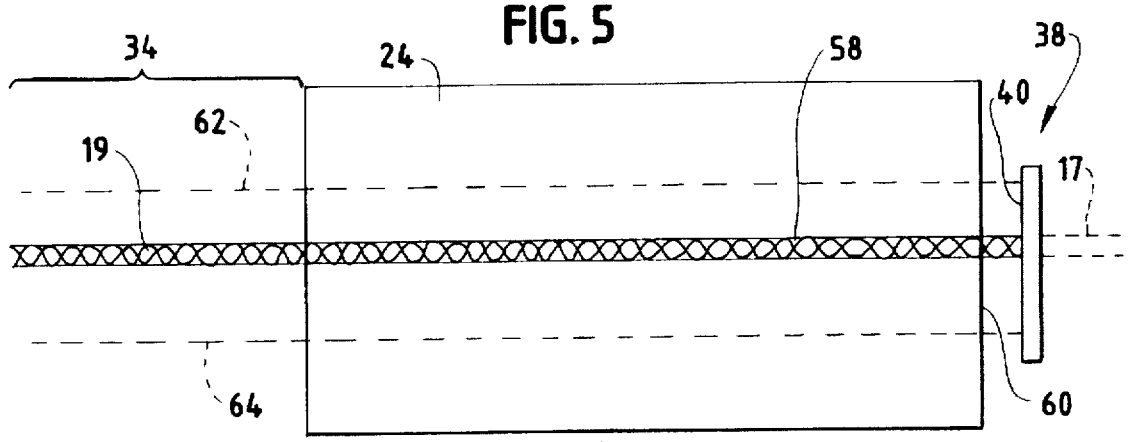
FIG. 5 is a side view of the downstream portion of the photodetachment region shown in FIG. 3B.
Figure 6:
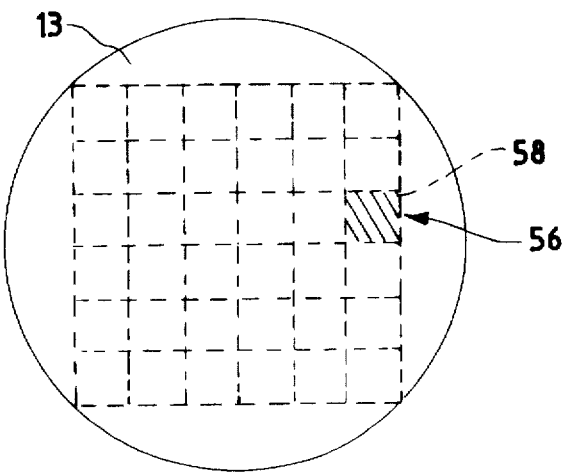
FIG. 6 is a cross-sectional view taken along line 6—6 in FIG. 3B of an H⁻ beam within the photodetachment region.

FIG. 6 is a cross-sectional view of the H⁻ beam 13 with a square central subsection therein being denoted in dashed lines. This rectangular subsection is representative of the 36 potential subsections through which the scanning laser 19 may pass. In the example of FIG. 6, subsection 56 is represented as receiving the laser beam 19 when the scanner 36 turns on electro-optic element #18 (FIG. 4). While electro-optic element #18 is on, the laser beam 19 passes through the photodetachment region 36 within subsection 56 of the H⁻ beam 13 (FIG. 6) until contacting the reflective coating 40 of stripping foil 38. The laser beam 19 is then reflected back onto itself along the common laser axis 44 again passing through subsection 56 of the H⁻ beam 13 until reaching the scanner 36. When the laser beam 19 passes through subsection 56 in the reverse direction, the photons within the scanning beam 19 deliver sufficient energy to the H⁻ ions within the subsection 56 of the H⁻ beam 13 to effect photodetachment of at least one electron from each ion. Photodetachment may not be caused by the photons traveling in the forward direction since the photons traveling in the same direction as the H⁻ beam 13 experience or a Doppler shift down to an energy which is below the photodetachment threshold. FIG. 5 is a side view of the downstream section of the photodetachment region 34 and of the downstream bent magnet 24. The laser beam 19 and corresponding neutral beam 58 for electro-optic element #18 are located at an intermediate point between the top and bottom edges 62 and 64 of the H⁻ beam 13. After photodetachment, the subsection 56 of the H⁻ beam 13 represents a charge changed section (also referred to as a neutral beam).

According to the photodetachment process, a moving H⁻ ion sees a change in photon energy, from a laser beam traveling in an opposite direction, given by the Doppler formula:

$$E = E_{laser}\, \gamma(1+\beta\cos\sigma)$$

where β and γ are the normal relativistic factors representing the energy of the traveling H⁻ beam, $E_{laser}$ is the single photon energy of the laser, and σ is the angle between the laser beam and the H⁻ beam. In the preferred embodiment, photodetachment occurs between the reflected laser beam and the oncoming H⁻ beam. Accordingly, σ=0 in this head-on collision represents the lowest single photon energy required for photodetachment and corresponds to the lowest laser power.

In most applications, the kinetic energy of the H⁻ beam may be less than 500 MeV, and thus a laser such as a Nd:YAG laser with a proton energy of 1.16 eV is well matched to the peak of the photodetachment reaction.

Returning to FIG. 3B, once the neutral beam 58 is formed through photodetachment within subsection 56, the complete H⁻ beam 13 and neutral beam pass to the second dipole magnet 24. The dipole magnet 24 generates a magnetic field which guides the H⁻ beam 13 to follow the contour of the accelerator. However, the neutral beam 46 in section 56 of the H⁻ beam 13 no longer is negatively charged, and thus is unaffected by the field induced within the magnet 24. Accordingly, the neutral beam 46 continues along a path parallel to and centered upon the laser axis 44. The neutral beam 46 is emitted from a discharge port 60 of the magnet 24. The neutral beam 46 collides with the stripping foil 38. The stripping foil 38 strips the remaining electron from each hydrogen atom, thereby delivering a proton beam 17 at its discharge side. As shown in FIG. 1, the proton beam 17 is then passed through quadrupoles 48 and a conveyance module 18 to be delivered to a remote patient station 20.

The conveyance module 18 may include static magnets 21 and 23 (FIG. 1) which cooperate to redirect an incoming proton beam 17 along a predefined trajectory. It is understood that the static magnets 21 and 23 define a set of trajectories between the input and output ends of the magnets. Thus, a proton beam entering the magnets 21 and 23 along a first input trajectory will be emitted therefrom at a known first output location corresponding to the first input trajectory. Similarly, a proton beam entering the static magnets along a second input trajectory will be emitted at a known second output location corresponding to the second input trajectory (which differs from the first input trajectory). The trajectory of the proton beam 17 followed through the static magnets 21 and 23 is dependent upon the initial or extraction trajectory of the proton beam 17 from the module 16. A proton beam 17 being generated from subsection 56 (FIG. 6) of the H⁻ beam 13 is incident upon the static magnets 21 and 23 at a corresponding input trajectory, and in turn relayed to a corresponding target at the patient station.

Figure 7:
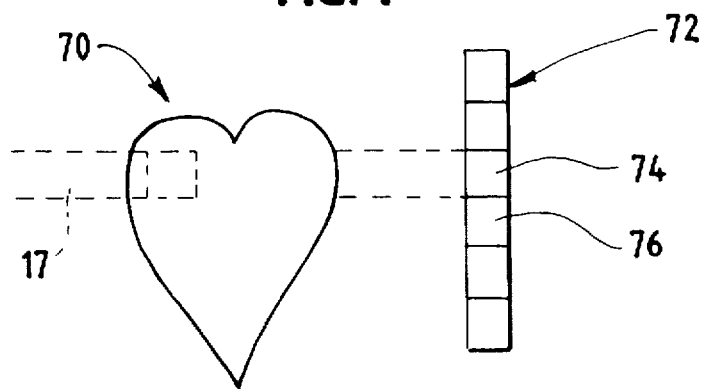
FIG. 7 is a patient treatment station in which the invented system is utilized in a proton radiography application.
Figure 8:
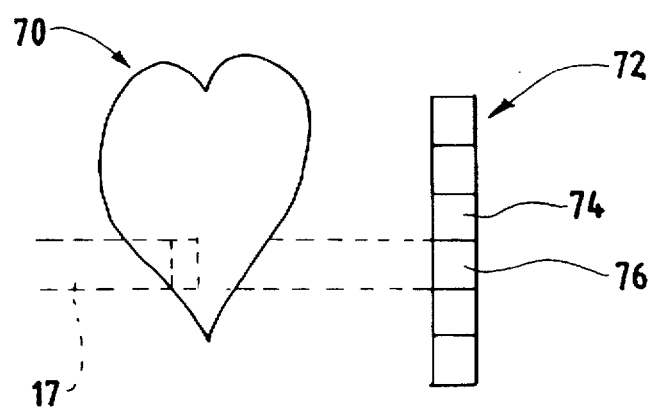
FIG. 8 is a patient treatment station in which the invented system is utilized in a proton radiography application.

FIGS. 7 and 8 illustrate an exemplary embodiment whereby the inventive system is utilized in connection with cardiography, namely, proton imaging of the organ 70. A proton sensitive imaging sensor 72 is placed behind the patient to sense incoming proton beams 17. The proton beam 17 is scanned across the organ 70 as the scanning beam 19 is moved across the H⁻ beam 13. For instance, FIG. 7 illustrates the proton beam 17 as incident upon a region 74 of the imaging sensor 72 which may result from any one of electro-optic elements #13–#18 (FIG. 4) being turned on. Similarly, proton beam 17 (FIG. 8) will be incident upon a region 76 of the imaging sensor 72 when one of the electro-optic elements #19–#24 (FIG. 4) of the pockel cell 48 is turned on. Thus, as the pockel cell 48 is controlled to turn on the electro-optic elements #1–#36 in a scanning manner, the resulting proton beam 17 is similarly moved in a scanning manner across the organ 70 to be monitored. In a proton cardiography application, the resulting proton beam is scanned across an imaging sensor 72 to form an image of the heart.

The scanner 36 may be controlled to adjust the intensity of the scanning beam 19 by varying the transmissivity of the electro-optic elements 52. By varying the intensity of the scanning beam 19, the intensity of the resulting neutral beam 58 relative to the intensity of the H⁻ beam is similarly varied. A sensor 37 monitors the intensity of the pulses in the H⁻ beam 13 and delivers a representative detection signal to the scanner 36. Thus, when the H⁻ beam varies in intensity between pulses, the sensor 37 detects the variation and the scanner 36 adjust the intensity of the scanning beam 19 accordingly. For instance, if the H⁻ beam intensity increases between consecutive pulses, the scanner 36 may control corresponding electro-optic elements 52 to decrease the intensity of associated scanning beams 19. Hence, the resulting proton beam 17 maintains a constant intensity independent of pulse to pulse variations within the H⁻ beam 13.

Alternatively, the inventive system may be utilized in a cancer treatment application, whereby the imaging sensor 72 is omitted and the intensity of the proton beam 17 increased to a level necessary for cancer treatment. In this alternative embodiment, the proton beam 17 is moved in a desired manner across the tumor to be treated. Movement of the proton beam 17 is still controlled by the scanner 36 through operation of the pockel cell 18 to turn on and off selected electro-optic elements (illustrated in FIG. 4).

According to the foregoing, the inventive system provides not only highly accurate targeting of the proton beam upon the object to be treated or imaged but also instantaneous intensity modulation which is critical to administering a correct total dose. The inventive system further enables extremely fast scanning of the object to be imaged, while retaining high resolution.

It is to be understood that the above described preferred embodiment is only by way of example and is not to be limiting. For instance, the pockel cell 48 may be omitted and any similar control structure substituted therefor so long as it provides the desired control of the scanning beam 19. Similarly, the bending magnets 22 and 24 and static magnets 21 and 23 may be removed and equivalent structure substituted therefor so long as the equivalent structure presents a photodetachment region 34 through which the incident scanning beam 19 may be projected to effect photodetachment and scanning and targeting at the patient station. Targeting of the scanning beam may be performed using photo diode arrays, or other light and intensity-sensitive detectors, to achieve a laser beam to target alignment which is accurate and reproducible to approximately 0.1 mr. With increased sophistication in the light and intensity-sensitive equipment, greater alignment accuracy will be possible.

Using static magnets 21 and 23 enables consistent and reliable operation and targeting of the proton beam at the patient station. In addition, the use of static magnets inherently simplifies the power supply design and specification therefore, thereby greatly reducing the overall cost of the facility. It is to be understood that the conveyance module 18 may be modified to achieve magnification or reduction of the pattern formed by the proton beams at the patient center. Alternatively, pulse magnets may be substituted for the bending magnets 22 and 24 and/or the static magnets 21 and 23 in order to extract and transfer the proton beam to the patient station. Pulse magnets may be necessary where the accelerator presents energy variations within the incident H$^-$ beam 13 in a pulse to pulse basis.

Preferably, the photodetachment region 34 may be a meter in length to minimize the laser intensity requirements and the number of off-trajectory or background H$^-$ ions neutralized (i.e. ions not traveling on the selected trajectory, but still passing through the scanning beam 17). Reducing the laser intensity prolongs the lifetime of optical components and reduces the overall cost and stability in the laser source. To achieve the meter long photodetachment region, the stripping foil 38 is coated with a reflective layer to operate as a mirror to reflect the scanning beam directly into a head-on collision with the H$^-$ beam. Thus, the laser photodetachment region extends between the dipole magnets 22 and 24.

Alternatively, more elaborate schemes may be utilized to control the laser intensity using electro-optic crystals to enhance the raster scanning ability of the proton beam 17. A pixel array of crystals whose light polarization transmittance characteristics are controlled by applied signals, as can be done with LCD technology, can be used to quickly and finely modulate the intensity of polarized light from the laser source. With this application, a large diameter laser beam would be generated using magnifying optical components. Pockel cell crystals can be used to attain pico second control over laser pulses.

It is to be understood that the present invention may be used outside of the medical field for scanning objects other than living tissue.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A proton beam radiology system comprising:

an accelerator for accelerating H$^-$ ions to a desired energy level to produce an H$^-$ beam having a first cross-sectional area;

a laser source for generating a scanning laser beam;

a photodetachment module, located proximate to and extending along a predefined peripheral portion of said accelerator, for projecting said scanning laser beam onto a subsection of said cross-sectional area of said H$^-$ beam within a photodetachment region of said H$^-$ beam, said scanning laser beam causing photodetachment within said subsection to form a neutral beam in said subsection of said cross-sectional area, said photodetachment module producing a proton beam from said neutral beam, said photodetachment module emitting said proton beam along an extraction trajectory corresponding to a position of said neutral beam within said H$^-$ beam;

a conveyance segment for transporting said proton beam along a trajectory to a patient treatment facility which delivers said proton beam to a target location upon a patient; and a laser scanner, operative with said photodetachment module, for moving said scanning laser beam along a transverse scanning pattern within said H$^-$ beam, in order to adjust said extraction trajectory of said proton beam and to vary correspondingly a target location of said proton beam at said patient treatment facility.

2. A proton beam radiology system according to claim 1, wherein said scanner maintains said scanning laser beam parallel to said H$^-$ beam throughout said photodetachment region.

3. A proton beam radiology system according to claim 1, wherein said photodetachment module comprises a stripping foil, located proximate a downstream end thereof, said stripping foil receiving and converting said neutral beam to said proton beam.

4. A proton beam radiology system according to claim 1, wherein said conveyance segment comprises at least one static magnet to transport said proton beam along one of a fixed set of predefined trajectories based on said extraction trajectory of said proton beam from said photodetachment module, said static magnet delivering said proton beam along a fixed trajectory to deliver said proton beam to a corresponding target location.

5. A proton beam radiology system according to claim 1, further comprising a stripping foil having a reflective coating thereon, said foil being aligned along an axis of said H$^-$ beam within said photodetachment module, said coating reflecting said scanning laser beam in a reverse direction, said stripping foil stripping said neutral beam to produce a proton beam.

6. A proton beam radiology system according to claim 1, wherein said scanner comprises a pockel cell array of electro-optic elements aligned to receive said laser beam from said laser source, said scanner individually and selectively turning on and off said elements of said pockel cell array to emit said scanning laser beam in a raster pattern which traverses said H$^-$ beam.

7. A proton beam radiology system according to claim 1, wherein said scanner comprises a turning mirror for guiding said scanning laser beam along a raster pattern across said H$^-$ beam.

8. A proton beam radiology system according to claim 1, wherein said photodetachment module directs said scanning laser beam in a direction opposite to a direction of travel of said H$^-$ beam to induce head-on collisions therebetween within said subsection to provide photodetachment and to form said neutral beam.

9. A proton beam radiology system according to claim 1, wherein said photodetachment module comprises a bending magnet, proximate a downstream end thereof for redirecting said H$^-$ beam along a transfer path about a periphery of said accelerator without interfering with a trajectory of said neutral beam extending along an axis defined by said scanning laser beam.

10. A proton beam radiology system according to claim 1, wherein said photodetachment module aligns said laser beam and said H$^-$ beam along parallel axes and in substantially close proximity to one another.

11. A proton beam radiology method comprising the steps of:

producing an H$^-$ beam having a desired energy level and a first cross-sectional area;

generating a scanning laser beam;

projecting said scanning laser beam onto a subsection of said cross-sectional area of said H$^-$ beam, said scanning laser beam causing photodetachment within said subsection to form a neutral beam therein;

producing a proton beam from said neutral beam, said proton beam extending along an extraction trajectory corresponding to a position of said neutral beam within said H$^-$ beam;

transporting said proton beam along a trajectory to a patient treatment station and delivering said proton beam to a target location upon a patient;

moving said scanning laser beam along a scanning pattern within said H⁻ beam, in order to adjust said extraction trajectory of said proton beam and to vary correspondingly said target location of said proton beam at said patient station.

12. A proton beam radiology method according to claim 11, further comprising the step of maintaining said scanning laser beam parallel to said H⁻ beam throughout a photodetachment region of said H⁻ beam.

13. A proton radiology method according to claim 11, further comprising the step of stripping electrons from said neutral beam to form said proton beam.

14. A radiology method according to claim 11, wherein said transporting step comprises the substep of defining a fixed set of predefined trajectories along which said proton beam will pass, and conveying said proton beam along one of said fixed trajectories based upon an incoming trajectory of said proton beam, and delivering said proton beam to a corresponding target location.

15. A proton beam radiology method according to claim 11, further comprising the step of reflecting said laser beam at a downstream end of a photodetachment region in a reverse direction back upon itself and said subsection of said cross-sectional area of said H⁻ beam.

16. A proton beam radiology method according to claim 11, further comprising the step of individually and selectively turning off and on separate elements of a pockel cell array to emit said scanning laser beam therefrom in a raster pattern which traverses said H⁻ beam.

17. A proton beam radiology method according to claim 11, further comprising the step of interposing a turning mirror for guiding said scanning laser beam along a raster pattern across said cross-sectional area of said H⁻ beam.

18. A proton beam radiology method according to claim 11, further comprising the step of directing said scanning beam in a direction opposite to a direction of travel of said H⁻ beam to induce head-on collisions therebetween within said subsection to produce photodetachment and form said neutral beam.

19. A proton beam radiology system according to claim 11, further comprising the step of redirecting said H⁻ beam along a transfer path about a periphery of an accelerator without interfering with a trajectory of said neutral beam, said trajectory of said neutral beam extending along an axis defined by said scanning laser beam.

20. A proton beam radiology method according to claim 11, further comprising the step of aligning said scanning laser beam and said H⁻ beam along parallel axes aligned substantially close to one another.

* * * * *